United States Patent
Kuula et al.

(10) Patent No.: US 12,268,787 B2
(45) Date of Patent: Apr. 8, 2025

(54) COMPOSITION FOR USE IN THE TREATMENT OF URINARY OR FAECAL INCONTINENCE

(71) Applicant: Lignum Medical Oy, Helsinki (FI)

(72) Inventors: Jani Kuula, Espoo (FI); Eija Raussi-Lehto, Espoo (FI); Orlando Rojas, Espoo (FI); Rubina Ajdary, Espoo (FI); Tomi Mikkola, Espoo (FI)

(73) Assignee: Lignum Medical Oy, Helsinki (FI)

( * ) Notice: Subject to any disclaimer, the term of this patent is extended or adjusted under 35 U.S.C. 154(b) by 0 days.

(21) Appl. No.: 18/282,545

(22) PCT Filed: Jan. 28, 2022

(86) PCT No.: PCT/FI2022/050054
§ 371 (c)(1),
(2) Date: Sep. 18, 2023

(87) PCT Pub. No.: WO2022/195158
PCT Pub. Date: Sep. 22, 2022

(65) Prior Publication Data
US 2024/0165046 A1   May 23, 2024

(30) Foreign Application Priority Data
Mar. 16, 2021   (FI) .................................. 20217052

(51) Int. Cl.
| | |
|---|---|
| *A61K 9/70* | (2006.01) |
| *A61K 9/00* | (2006.01) |
| *A61K 31/717* | (2006.01) |
| *A61L 27/20* | (2006.01) |
| *A61L 27/54* | (2006.01) |

(52) U.S. Cl.
CPC .............. *A61K 9/70* (2013.01); *A61K 9/0024* (2013.01); *A61K 31/717* (2013.01); *A61L 27/20* (2013.01); *A61L 27/54* (2013.01); *A61L 2300/412* (2013.01); *A61L 2300/64* (2013.01); *A61L 2400/06* (2013.01); *A61L 2400/12* (2013.01);
(Continued)

(58) Field of Classification Search
CPC .............................. A61K 9/70; A61K 31/717
See application file for complete search history.

(56) References Cited

U.S. PATENT DOCUMENTS

| 12,077,915 B2* | 9/2024 | Retsina ................... D21C 3/20 |
| 2008/0311219 A1 | 12/2008 | Gosiewska et al. |
| 2020/0102426 A1* | 4/2020 | de Assis Dutra Melo ................. C08J 3/075 |

FOREIGN PATENT DOCUMENTS

| JP | 2017517478 A | 6/2017 |
| JP | 2022522997 A | 4/2022 |
| WO | WO2021245324 A1 | 12/2021 |

OTHER PUBLICATIONS

Ajdary et al: Acetylated Nanocellulose for Single-Component Bioinks and Cell Proliferation on 3D-Printed Scaffolds. Biomacromolecules, 2019, vol. 20, No. 7, pp. 2770-2778.
(Continued)

*Primary Examiner* — Carlos A Azpuru
(74) *Attorney, Agent, or Firm* — Laine IP Oy; Mark W. Scott

(57) ABSTRACT

According to an example aspect of the present invention, there is provided a composition for use in the treatment of urinary or faecal incontinence, the composition comprising a nanostructured cellulosic material.

26 Claims, 2 Drawing Sheets

(52) U.S. Cl.
CPC ....... *A61L 2430/22* (2013.01); *A61L 2430/34* (2013.01)

(56) References Cited

OTHER PUBLICATIONS

Brosche et al: Seven-year efficacy and safety outcomes of Bulkamid for the treatment of stress urinary incontinence. Neurourology and Urodynamics, 2021, vol. 40, pp. 502-508.

Chen et al: GVL pulping facilitates nanocellulose production from woody biomass. Green Chemistry, Sep. 30, 2019, vol. 21, No. 19, pp. 5316-5325.

Chunilall et al: Supra-Molecular Structure and Chemical Reactivity of Cellulose I Studied Using CP/MAS 13C-NMR. Cellulose—Fundamental Aspects, 2013, IntechOpen.

Curvello et al: Engineering Nanocellulose Hydrogels for Biomedical Applications. Adv. Colloid Interface Sci., 2019, vol. 267, pp. 47-61.

Isogai et al: Tempo-Oxidized Cellulose Nanofibers. Nanoscale, 2011, vol. 3, No. 1, pp. 71-85.

Keltie et al: Complications Following Vaginal Mesh Procedures for Stress Urinary Incontinence: An 8 Year Study of 92,246 Women. Sci. Rep., 2017, vol. 7, No. 1, pp. 1-9.

Li et al: Homogeneous isolation of nanocelluloses by controlling the shearing force and pressure in microenvironment. Carbohydrate Polymers, Applied Science Publishers, Jul. 11, 2014, vol. 113, pp. 389-393.

Maggiore et al: Urethral Bulking Agents versus Other Surgical Procedures for the Treatment of Female Stress Urinary Incontinence: A Systematic Review and Meta-Analysis. Eur. J. Obstet. Gynecol., Reprod. Biol., 2015, vol. 189, pp. 48-54.

Magon et al: Stress Urinary Incontinence: What, When, Why, and Then What? J. Midlife. Health, 2011, vol. 2, No. 2, p. 57.

Sharma et al: Commercial Application of Cellulose Nano-Composites—A Review. Biotechnol. Reports 2019, 2018, vol. 21, e00316.

U.S. Food and Drug Administration: Urogynecologic Surgical Mesh Implants. Retrieved from https://www.fda.gov/medical-devices/implants-and-prosthetics/urogynecologic-surgical-mesh-implants on Sep. 18, 2023.

Wang et al: Use of Bioactive Extracellular Matrix Fragments as a Urethral Bulking Agent to Treat Stress Urinary Incontinence. Acta Biomater, 2020, vol. 117, pp. 156-166.

Zacche et al: Changing Surgical Trends for Female Stress Urinary Incontinence in England. Int. Urogynecol. J., 2019, vol. 30, No. 2, pp. 203-209.

\* cited by examiner

COMPOSITION FOR USE IN THE TREATMENT OF URINARY OR FAECAL INCONTINENCE

FIELD

The present application relates to compositions for use in the treatment of urinary incontinence.

BACKGROUND

Urinary incontinence refers to unintentional leakage of urine. It has a considerable impact on the well-being of between 14.8-31.8% of women. Stress urinary incontinence (SUI) is the most common type of urinary incontinence of women, and also men. Stress urinary incontinence is a condition where leakage of urine occurs during physical activity that increases abdominal pressure. Physical activity can include coughing, sneezing, laughing, or physical exercise.

The reason behind the SUI is the weakening of the tissue supporting the bladder and/or urethra. This causes the group of muscles that connect the bladder to the urethra (bladder neck) to descend during physical activity. Once this descent occurs, the urethra, particularly, the wall of the urethra, does not work properly to control the urine not to leak from bladder.

Another mechanism for the SUI is that the sphincter muscle that controls the urethra weakens. In this condition the sphincter muscle cannot prevent the urine flow under high abdominal pressure or during physical activity that increases abdominal pressure.

Risk factors for the development of SUI are pregnancy, childbirth, aging, prior pelvic surgery, chronic coughing or straining, obesity and smoking.

Non-severe cases of SUI can be treated with pelvic floor muscle exercises, scheduled toileting and/or a healthier lifestyle including quitting smoking and losing weight.

Non-invasive medical devices to treat SUI include pessaries and tampon-like urethral inserts.

When surgical treatment is needed, the most common surgical approach is the sling procedure, where a surgeon places a mesh to support the urethra. The commonly used sling material and its insertion procedure are very invasive, and its safety has raised patients' concerns. Complications associated with mesh insertion include mesh erosion, pain, infection, and organ perforation. In 2019, The U.S. Food and Drug Administration (FDA) took action to support women's health and ordered an immediate stop in selling and distribution of transvaginal meshes due to the adverse reports associated with the use of surgical meshes.

A less invasive and a lower-risk method is to use a bulking agent that is injected around the urethra. The idea with the bulking agent is to improve the closing capability of the sphincter by bulking up the urethra by using the bulking agent material. Although the action of bulking agents is relatively short-term, the low invasiveness of the treatment eases the repeatability of the procedure considering the reduced post-operative adverse immune response. However, the bulking agents reported in the literature have shown low efficiencies:

Brosche, T.; Kuhn, A.; Lobodasch, K.; Sokol, E. R. Seven-Year Efficacy and Safety Outcomes of Bulkamid for the Treatment of Stress Urinary Incontinence. Neurourol. Urodyn. 2021, 40 (1), 502-508.

Leone Roberti Maggiore, U.; Bogani, G.; Meschia, M.; Sorice, P.; Braga, A.; Salvatore, S.; Ghezzi, F.; Serati, M. Urethral Bulking Agents versus Other Surgical Procedures for the Treatment of Female Stress Urinary Incontinence: A Systematic Review and Meta-Analysis. Eur. J. Obstet. Gynecol. Reprod. Biol. 2015, 189, 48-54.

Embodiments of the present invention are intended to overcome at least some of the disadvantages in the prior art.

SUMMARY OF THE INVENTION

The invention is defined by the features of the independent claims. Some specific embodiments are defined in the dependent claims.

According to a first aspect of the present invention, there is provided a composition for use in the treatment of urinary or faecal incontinence, the composition comprising a nanostructured cellulosic material.

Various embodiments of the first aspect may comprise one or more features from the following bulleted list:

- The nanostructured cellulosic material comprises or consists of never-dried nanostructured cellulosic material,
- The nanostructured cellulosic material comprises or consists of bleached never-dried nanostructured cellulosic material.
- The nanostructured cellulosic material comprises or consists of nanofibrillated cellulose (NFC).
- The nanostructured cellulosic material comprises or consists of cross-linked nanostructured cellulosic material, such as ionically or physically or chemically cross-linked nanostructured cellulosic material.
- The nanostructured cellulosic material comprises cellulosic fibres having a width-average fibre width in the range 10 to 100 nm, such as in the range 20 to 50 nm.
- The nanostructured cellulosic material comprises cellulosic fibres having a length-average fibre length of at least 100 µm, such as in the range 100 to 1 000 µm.
- The nanostructured cellulosic material comprises cellulosic fibres having a length-to-width aspect ratio of at least 2 000, such as at least 10 000.
- The composition is in the form of an aqueous gel, such as an injectable aqueous gel, typically in room temperature and/or in human body temperature.
- The composition comprises 0.5 to 2.0 wt-% of a nanostructured cellulosic material.
- The composition comprises at least 95 wt-%, such as at least 98 wt-%, such as at least 99 wt-% water.
- The composition comprises one or more active substances, such as a tissue growth enhancing substance.
- The composition comprises live cells or a substance preventing or reducing repelling of the composition by the mammal's body.
- The composition is shear-thinning, typically in room temperature.
- The nanostructured cellulosic material has been modified to increase hydrophilicity or hydrophobicity of the cellulosic fibres therein, for example by introducing or attaching charged functional groups on surfaces of the cellulosic fibres.
- The nanostructured cellulosic material has been modified to prevent or reduce aggregation of the composition during injection of the composition into a mammalian tissue, such as inside a wall of the urethra of a mammal, for example under the mucosa of the urethra.
- The composition is for use in the treatment of urinary incontinence, such as stress urinary incontinence (SUI) or stress-predominant mixed urinary incontinence (MUI), or faecal incontinence, preferably stress urinary incontinence (SUI).

The composition is for use in the treatment of urinary incontinence as a bulking agent which is configured to be injected inside a wall of the urethra of a mammal, for example under the mucosa of the urethra, preferably to improve closing of the sphincter.

The composition is for use in the treatment of stress-predominant mixed urinary incontinence (MUI) as a bulking agent.

The composition is for use in the treatment of faecal incontinence as a bulking agent.

The composition is for use in the treatment of faecal incontinence as a bulking agent which is configured to be injected inside a wall of the rectum of a mammal, preferably to improve closing of the sphincter.

The composition has been obtained by a method comprising: providing a cellulosic material; delaminating or fibrillating the cellulosic material, particularly cell walls of the cellulose, to obtain a nanostructured cellulosic material, such as nanofibrillated cellulose; preparing an aqueous composition from the obtained nanostructured cellulosic material, wherein the composition comprises at least 2 wt-% nanostructured cellulosic material and at least 95 wt-% water.

Said delaminating step is carried out by a microfluidizer, such as a high-pressure microfluidizer, preferably at a pressure of at least 1 400 bars.

The method further comprises refining the cellulosic material.

According to a second aspect of the present invention, there is provided a method for treatment of urinary incontinence, preferably stress urinary incontinence, in a mammal, preferably a human, the method comprising: providing the composition according to the first aspect; injecting the composition in a gel form into a wall of the urethra of the mammal, for example under the mucosa of the urethra, to create a submucosal cushioning inside the wall of the urethra.

According to a third aspect of the present invention, there is provided a method for treatment of faecal incontinence in a mammal, preferably a human, the method comprising: providing the composition according to the first aspect; injecting the composition in a gel form into a wall of the rectum of the mammal to create a submucosal cushioning inside the wall of the rectum.

Advantages

The present invention may provide an improved and more effective bulking agent for treatment of urinary or faecal incontinence.

The present invention may provide a highly biocompatible bulking agent.

The present invention may provide a non-synthetic biomaterial that is non-toxic and suitable for use as a bulking agent.

The present bulking agent material typically does not degrade naturally in the body and may perform as a sustainable bulking agent.

In some embodiments, aggregation, stability and/or processability problems related to known bulking agents may be alleviated.

The present material is preferably sterilisable, such as by autoclave or steam sterilization.

BRIEF DESCRIPTION OF THE DRAWINGS

FIG. 1(a) shows the cellulose fibers before microfluidization. FIG. 1(b) shows the nanocellulose obtained after one pass in microfluidization at the pressure of 1400 bars. FIG. 1(c) shows the transmission electron microscopy of nanocellulose and the visualization of the physical entanglements of high aspect ratio nanofibrils. FIG. 1(d) shows the viscosity profile of nanocellulose and the dependency of viscosity profile on the concentration of nanocellulose.

FIG. 2(a) shows the oscillatory rheological behaviour of nanocellulose at 0.5 wt-% and 2.0 wt-%, FIG. 2(b) shows the storage and loss modulus of nanocellulose (frequency sweep conducted at a constant strain of 0.5%, and a fixed gap of 0.5 mm). FIG. 2(c) shows extrusion of NFC, FIG. 2(d) shows non-crosslinked NFC, and FIG. 2(e) shows metal-ion crosslinked NFC.

EMBODIMENTS

Definitions

Figure 1:
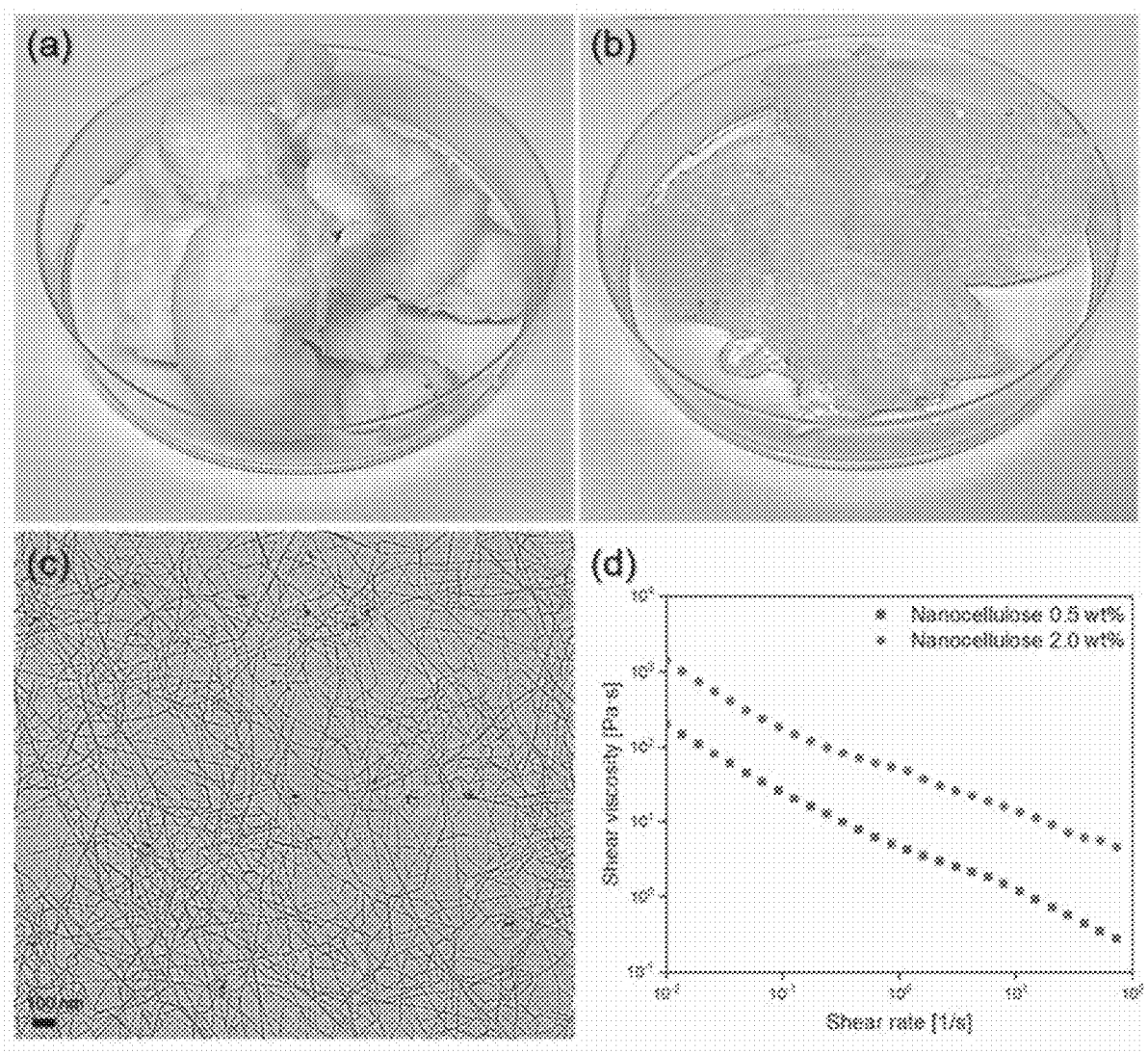
FIGS. 1(a) to 1(d) illustrate cellulosic raw materials and end products and their viscosity properties in a method in accordance with at least some embodiments of the present invention.

Unless otherwise stated herein or clear from the context, any percentages referred to herein are expressed as percent by weight based on a total weight of the respective composition.

As used herein, unless otherwise stated, the term "viscosity" stands for dynamic viscosity, at 25° C., and has been determined by a rheometer at shear rates 0.01 to 100 s$^{-1}$.

As used herein, the term "treatment" or "treating" refers to administration of the composition of the invention to a subject, e.g., a mammal or human subject, for purposes which include not only complete cure, but also prophylaxis, amelioration, or alleviation of a disorder or symptoms related to a pathological condition. The therapeutic effect may be assessed by monitoring the symptoms of a patient, biomarkers in blood, a size of an injury or lesion, and/or or the length of survival of the patient.

In the present context, the terms "nanostructured cellulose" and "nanocellulose" and "nanofibrillated cellulose" may be used interchangeably and typically refer to cellulose that has at least one dimension, preferably all three dimensions, in nanoscale, particularly 1 to 100 nm.

By "never-dried cellulose" it is referred to a cellulosic material which has not undergone any drying step during its manufacturing process, such as a pulping process.

Unless otherwise indicated, fibre length was determined by means of the L&W Fiber Tester Plus instrument.

Unless otherwise indicated, fibre width (fibre diameter) and fibre shape were determined from SEM images.

In the present context, length-average fibre length is measured and defined according to the standard ISO 16065-2.

It has been observed that nanocellulose gel may be used as a bulking agent to treat for example urinary incontinence. Nanocellulose is a non-synthetic biomaterial that is non-toxic and is highly biocompatible. Nanocellulose does not degrade naturally in the body and can perform as a sustainable bulking agent.

Some embodiments of the present invention provide methods involving injection of (nano)cellulose gel into the wall of urethra of humans and other mammals to treat urinary incontinence in order to prevent urine from leaking from the bladder creating an artificial cushioning around the urethra with or without releasing tissue growth enhancing substance.

Some embodiments of the present invention provide methods for treating faecal incontinence.

Typically, the invention concerns a composition for use in the treatment of urinary or faecal incontinence, the composition comprising a nanostructured cellulosic material.

The nanostructured cellulosic material may comprise or consist of never-dried nanostructured cellulosic material, preferably bleached never-dried nanostructured cellulosic material.

The nanostructured cellulosic material may comprise or consist of nanofibrillated cellulose (NFC).

In one embodiment, the nanostructured cellulosic material comprises cellulosic fibres having a width-average fibre width of at least 10 nm, such as in the range 10 to 100 nm, such as in the range 20 to 50 nm.

In one embodiment, the nanostructured cellulosic material comprises cellulosic fibres having a length-average fibre length of at least 50 μm, such at least 100 μm, such as at least 500 μm, or for example in the range 100 to 1 000 μm.

In one embodiment, the nanostructured cellulosic material comprises cellulosic fibres having a length-to-width aspect ratio of at least 2 000, such as at least 5 000, such as at least 7 000, for example at least 10 000.

The composition is typically in the form of an aqueous gel, such as an injectable aqueous gel in room temperature and/or in human body temperature.

The composition may comprise 0.5 to 2.0 wt-% of a nanostructured cellulosic material, of total weight of the composition.

Preferably, the composition is in the form of an aqueous composition, such as an aqueous gel, comprising at least 95 wt-% water, such as at least 97 wt-% water, for example at least 99 wt-% water.

The composition may comprise one or more active substances, such as a tissue growth enhancing substance or live cells.

Typically the composition is shear-thinning, which usually improves its injectability into a body.

In some embodiments, the composition is obtained by a method comprising: providing a cellulosic material; delaminating the cellulosic material, particularly cell walls of the cellulose, to obtain a composition comprising a nanostructured cellulosic material, such as nanofibrillated cellulose; preparing an aqueous composition from the obtained nanostructured cellulosic material, wherein the composition comprises at least 2 wt-% nanostructured cellulosic material and at least 95 wt-% water.

In one embodiment, said delaminating step is carried out by a high-pressure microfluidizer, preferably at a pressure of at least 1 000 bar, such as at least 1 400 bar.

In one embodiment, the method further comprises refining the cellulosic material.

FIG. 1(a) shows cellulose fibres before microfluidization and FIG. 1(b) shows nanocellulose obtained after 1 pass in microfluidization at a pressure of 1 400 bars. FIG. 1(c) shows transmission electron microscopy of nanocellulose and the visualization of the physical entanglements of high aspect ratio nanofibrils. FIG. 1(d) shows the viscosity profile of nanocellulose and the dependency of the viscosity profile on the concentration of nanocellulose.

Cellulose is the most abundant natural polymer that is renewable, biodegradable, biocompatible and non-toxic. Never-dried bleached cellulose fibres (FIG. 1(a)) may be processed mechanically in a high-pressure fluidizer to delaminate the cellulose cell wall and to produce nanostructured cellulose (nanofibrillated cellulose, NFC) with width dimensions of 20-50 nm and length of several hundred microns (FIGS. 1(b) and 1(c)). The high aspect ratio of nanocellulose contributes to enhanced entanglement of the nanofibrils and stability in wet condition.

NFC has the pseudo-plastic property, meaning that the material forms a thick gel in normal condition or in low concentrations. The viscosity of nanocellulose is adjustable by changing the concentration of the gel (by adding or removing water) and by refining the gel to break the fibrils and to obtain shorter and thinner nanofibrils. Nanocellulose is highly hydrophilic with the surface containing many hydroxyl groups. The gel may contain more than 99% water and still displaying the shear-thinning behaviour as indicated in FIG. 1(d). This behaviour makes nanocellulose to be easily injectable with a wide range of needle sizes.

As indicated in FIG. 2(a), the storage modulus>loss modulus (G'>G") confirms the gel-like behaviour in NFC in a wide range of studied shear stresses. In addition, nanocellulose demonstrates a dominant elastic behaviour with G'>G", with about an order of magnitude higher storage modulus than the loss modulus. The rheological properties of NFC verify its suitability for injection purposes. FIGS. 2(c) to 2(e) display the extrusion of NFC in the form of 1D filaments and 3D structures to show the potential of NFC as a stable gel.

Figure 2:
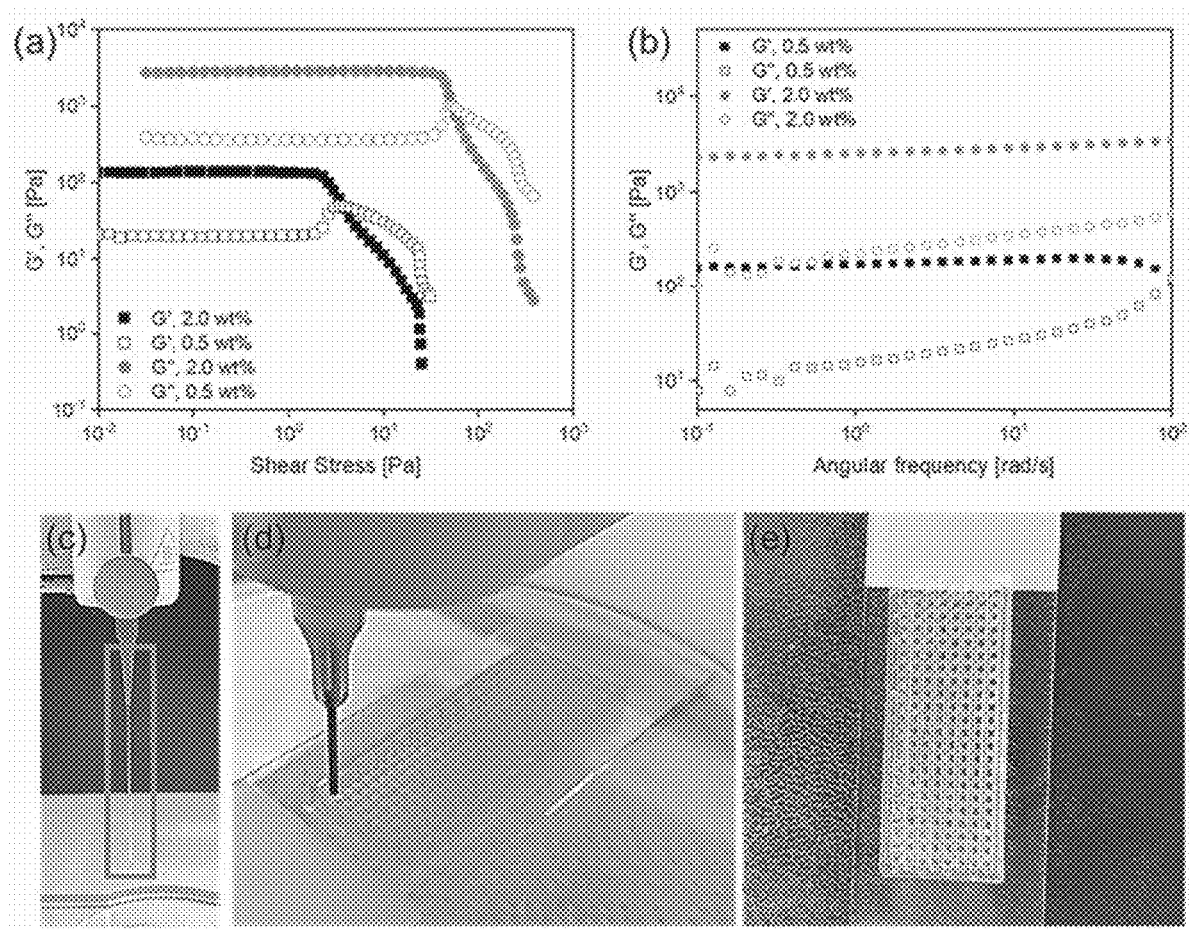
FIG. 2 demonstrates the linear viscoelastic region (based on storage modulus (G') and loss modulus (G")).

In the embodiments illustrated in the FIGS. 1 and 2, the nanocellulose was not modified by a separate modifying step.

In the following, we describe methods to modify the nanocellulose according to some embodiments.

The surface of nanocellulose can be modified to be more hydrophilic or less hydrophilic according to the desired application. This modification is done by introducing surface charges to nanocellulose. Presence of surface charges decreases the gel aggregation and enhances the processability of the gel and the stability of the gel after injection.

The glucose units in cellulose contain three different hydroxyl groups (O(2)H, O(3)H, and O(6)H), which are capable of participating in a variety of chemical reactions.

At least part of the surfaces of the nanocellulose may be modified to be more hydrophilic, for example by 2,2,6,6-tetramethylpiperidine-1-oxy (TEMPO) mediated oxidation, to introduce carboxyl groups to the backbone of the nanocellulose, such as nanofibrillated cellulose. Suitable exemplary methods for modification of nanocellulose are disclosed in: Isogai, A.; Saito, T.; Fukuzumi, H. TEMPO-Oxidized Cellulose Nanofibers. Nanoscale 2011, 3 (1), 71-85.

Also, at least part of the surfaces of the nanocellulose may be modified to be less hydrophilic, for example by an acetylation process to introduce acetyl groups to the backbone of the nanocellulose, such as nanofibrillated cellulose.

These modifications introduce surface charges to the nanocellulose. The presence of surface charges may decrease the nanocellulose gel aggregation during injection into a body. It may also enhance the processability of the gel and/or the stability of the gel after injection.

In one embodiment, an easy approach to adjust or fine-tune the viscosity of the nanocellulose, such as nanofibrillated cellulose, is by physical and/or chemical crosslinking.

Ionic cross-linking of the nanocellulose, such as nanofibrillated cellulose, may be carried out by metal ions, such as $Ca^{2+}$, $Zn^{2+}$, $Cu^{2+}$, $Al^{3+}$ and/or $Fe^{3+}$. The ionic cross-linking may increase the viscosity of the soft NFC. The ionic cross-linking may enhance the toughness and stiffness by increasing the surface charge density. The cross-linking typically occurs quickly upon the interaction of NFC and metal ion salts, and the mechanical performance of the gel varies depending on the type of used metal ions, typically improving in the order zinc ion<calcium ion<aluminium ion. Mentioned cross-linking approaches (physical or chemical) may be applied to modify the viscoelastic properties of NFC and develop customized bulking agents to treat SUI.

In one embodiment, the nanostructured cellulosic material has been modified to increase hydrophilicity of the material, particularly hydrophilicity of cellulose or cellulosic fibres in the material. This may be accomplished for example by attaching carboxyl groups onto the fibres.

In one embodiment, the nanostructured cellulosic material has been modified to increase hydrophobicity of the material, particularly hydrophobicity of cellulose or cellulosic fibres in the material. This may be accomplished for example by attaching acetyl groups onto the fibres.

In one embodiment, fibre surfaces of the nanostructured cellulosic material have been modified to increase their surface charge density.

In one embodiment, the nanostructured cellulosic material comprises cross-linked nanostructured cellulosic material.

In one embodiment, the nanostructured cellulosic material comprises ionically cross-linked nanostructured cellulosic material. The ionic cross-linking may be carried out by metal ions, such as metal ion salts.

The metal ion salt may be selected from the following: sodium chloride, calcium chloride, and mixtures thereof.

In one embodiment, the nanostructured cellulosic material comprises physically cross-linked nanostructured cellulosic material.

In one embodiment, the nanostructured cellulosic material comprises chemically cross-linked nanostructured cellulosic material.

Application Areas of the Present Composition

The composition is preferably for use in the treatment of stress urinary incontinence (SUI), stress-predominant mixed urinary incontinence (MUI) or faecal incontinence, most preferably stress urinary incontinence (SUI).

In some embodiments, the composition is for use in the treatment of urinary incontinence, preferably stress urinary incontinence (SUI), as a bulking agent which is configured to be injected inside a wall of the urethra of a mammal, preferably to improve closing of the sphincter.

Some embodiments provide a method for treatment of urinary incontinence in a mammal, the method comprising: providing a composition comprising a nanostructured cellulosic material; injecting the composition in a gel form into a wall of the urethra of the mammal, to create a submucosal cushioning inside a wall of the urethra, for example under the mucosa of the urethra.

Some embodiments provide a method for treatment of faecal incontinence in a mammal, preferably a human, the method comprising: providing a composition comprising a nanostructured cellulosic material; injecting the composition in a gel form into a wall of the rectum of the mammal, to create a submucosal cushioning inside the wall of the rectum.

Typically, the obtained cushioning inside the wall of the urethra or the rectum is and remains soft and stable in the wall of the urethra after the injection, typically for long periods of times, for example at least 1 year, such as at least 5 years.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", i.e. a singular form, throughout this document does not exclude a plurality.

INDUSTRIAL APPLICABILITY

The present invention is industrially applicable at least in the manufacturing of compositions for use in the treatment of urinary incontinence.

ACRONYMS LIST

SUI stress urinary incontinence
MUI stress-predominant mixed urinary incontinence
NFC nanofibrillated cellulose

CITATION LIST

Non Patent Literature

Zacche, M. M.; Mukhopadhyay, S.; Giarenis, I. Changing Surgical Trends for Female Stress Urinary Incontinence in England. Int. Urogynecol. J. 2019, 30 (2), 203-209.

Magon, N.; Malik, S.; Kalra, B.; Chauhan, M. Stress Urinary Incontinence: What, When, Why, and Then What? J. Midlife. Health 2011, 2 (2), 57.

Keltie, K.; Elneil, S.; Monga, A.; Patrick, H.; Powell, J.; Campbell, B.; Sims, A. J. Complications Following Vaginal Mesh Procedures for Stress Urinary Incontinence: An 8 Year Study of 92,246 Women. Sci. Rep. 2017, 7 (1), 1-9.

Administration, F. and D. Urogynecologic Surgical Mesh Implants https://www.fda.gov/medical-devices/implants-and-prosthetics/urogynecologic-surgical-mesh-implants.

Wang, Y.; Duan, M.; Rahman, M.; Yang, M.; Zhao, W.; Zhou, S.; Gao, G.; Fu, Q. Use of Bioactive Extracellular Matrix Fragments as a Urethral Bulking Agent to Treat Stress Urinary Incontinence. Acta Biomater. 2020, 117, 156-166.

Brosche, T.; Kuhn, A.; Lobodasch, K.; Sokol, E. R. Seven-Year Efficacy and Safety Outcomes of Bulkamid for the Treatment of Stress Urinary Incontinence. Neurourol. Urodyn. 2021, 40(1), 502-508.

Leone Roberti Maggiore, U.; Bogani, G.; Meschia, M.; Sorice, P.; Braga, A.; Salvatore, S.; Ghezzi, F.; Serati, M. Urethral Bulking Agents versus Other Surgical Procedures for the Treatment of Female Stress Urinary Incontinence: A Systematic Review and Meta-Analysis. Eur. J. Obstet. Gynecol. Reprod. Biol. 2015, 189, 48-54.

Ajdary, R.; Huan, S.; Zanjanizadeh Ezazi, N.; Xiang, W.; Grande, R.; Santos, H. A.; Rojas, O. J. Acetylated Nanocellulose for Single-Component Bioinks and Cell Proliferation on 3D-Printed Scaffolds. Biomacromolecules 2019, 20 (7), 2770-2778.

Sharma, A.; Thakur, M.; Bhattacharya, M.; Mandal, T.; Goswami, S. Commercial Application of Cellulose Nano-Composites—A Review. Biotechnol. Reports 2019, 21 (2018), e00316.

Chunilall, V.; Bush, T.; Larsson, P. T. Supra-Molecular Structure and Chemical Reactivity of Cellulose I Studied Using CP/MAS 13C-NMR. In Cellulose—Fundamental Aspects; Van De Ven, T. G. M., Godbout, L., Eds.; IntechOpen, 2013.

Isogai, A.; Saito, T.; Fukuzumi, H. TEMPO-Oxidized Cellulose Nanofibers. Nanoscale 2011, 3 (1), 71-85.

Curvello, R.; Raghuwanshi, V. S.; Garnier, G. Engineering Nanocellulose Hydrogels for Biomedical Applications. Adv. Colloid Interface Sci. 2019, 267, 47-61.

The invention claimed is:

1. A composition for use as a bulking agent, which is configured to be injected inside a wall of the urethra of a mammal or inside a wall of the rectum of a mammal, in the treatment of urinary or faecal incontinence respectively, the composition comprising a nanostructured cellulosic material,
   wherein the composition comprises 0.5 to 5.0 wt-% of the nanostructured cellulosic material and at least 95 wt-% water,
   wherein the nanostructured cellulosic material comprises never-dried nanostructured cellulosic material which has been manufactured by a pulping process,
   wherein the nanostructured cellulosic material comprises cellulosic fibres having a length-to-width aspect ratio of at least 500.

2. The composition according to claim 1, wherein the nanostructured cellulosic material comprises or consists of bleached never-dried nanostructured cellulosic material.

3. The composition according to claim 1, wherein the nanostructured cellulosic material comprises or consists of cross-linked nanostructured cellulosic material.

4. The composition according to claim 1, wherein the nanostructured cellulosic material comprises cellulosic fibres having a width-average fibre width in the range 10 to 100 nm.

5. The composition according to claim 1, wherein the nanostructured cellulosic material comprises cellulosic fibres having a length-average fibre length of at least 100 µm.

6. The composition according to claim 1, which is in the form of an injectable aqueous gel, when at room temperature or at human body temperature.

7. The composition according to claim 1, wherein the composition comprises 0.5 to 2.0 wt-% of the nanostructured cellulosic material.

8. The composition according to claim 1, wherein the composition comprises at least 97 wt-% water.

9. The composition according to claim 1, wherein the composition further comprises a tissue growth enhancing substance or live cells.

10. The composition according to claim 1, wherein the composition is shear-thinning.

11. The composition according to claim 1, wherein the nanostructured cellulosic material has been modified to increase hydrophilicity or hydrophobicity of the cellulosic fibres by introducing or attaching charged functional groups on surfaces of the cellulosic fibres.

12. The composition according to claim 1, wherein the nanostructured cellulosic material has been modified to prevent or reduce aggregation of the composition during injection of the composition into a mammalian tissue.

13. The composition according to claim 1, for use in the treatment of stress urinary incontinence (SUI), stress-predominant mixed urinary incontinence (MUI) or faecal incontinence.

14. The composition according to claim 1, for use in the treatment of stress urinary incontinence (SUI) as a bulking agent which is configured to be injected inside a wall of the urethra of a mammal to improve closing of the sphincter.

15. The composition according to claim 1, obtained by a method comprising:
   providing a cellulosic material;
   delaminating the cellulosic material to obtain nanofibrillated cellulose;
   preparing an aqueous composition from the obtained nanofibrillated cellulose.

16. The composition according to claim 15, wherein said delaminating step is carried out by a high-pressure microfluidizer at a pressure of at least 1,400 bars.

17. The composition according to claim 15, wherein the cellulose material comprises refined cellulosic material.

18. The composition according to claim 1, wherein at least part of the surfaces of the nanostructured cellulosic material has been modified to be more hydrophilic by 2,2,6,6-tetramethylpiperidine-1-oxy (TEMPO) mediated oxidation, to introduce carboxyl groups to the backbone of the nanostructured cellulosic material.

19. The composition according to claim 1, wherein nanostructured cellulosic material comprises nanofibrillated cellulose (NFC).

20. The composition according to claim 1, wherein the nanostructured cellulosic material has been manufactured by a process consisting of a pulping process.

21. The composition according to claim 1, wherein the nanostructured cellulosic material comprises nanostructured cellulosic material ionically cross-linked with metal ions.

22. The composition according to claim 1, wherein the nanostructured cellulosic material comprises cellulosic fibres having a width-average fibre width in the range 20 to 50 nm.

23. The composition according to claim 1, wherein the nanostructured cellulosic material comprises cellulosic fibres having a length-average fibre length of from 100 μm to 1000 μm.

24. A composition for use as a bulking agent, which is configured to be injected inside a wall of the urethra of a mammal or inside a wall of the rectum of a mammal, in the treatment of urinary or faecal incontinence respectively, the composition comprising a nanostructured cellulosic material,
   wherein the composition comprises 0.5 to 5.0 wt-% of the nanostructured cellulosic material and at least 95 wt-% water,
   wherein the nanostructured cellulosic material comprises never-dried nanostructured cellulosic material which has been manufactured by a pulping process, and
   wherein the nanostructured cellulosic material comprises cellulosic fibres having a width-average fibre width in the range 10 to 100 nm.

25. A composition for use as a bulking agent, which is configured to be injected inside a wall of the urethra of a mammal or inside a wall of the rectum of a mammal, in the treatment of urinary or faecal incontinence respectively, the composition comprising a nanostructured cellulosic material,
   wherein the composition comprises 0.5 to 5.0 wt-% of the nanostructured cellulosic material and at least 95 wt-% water,
   wherein the nanostructured cellulosic material comprises never-dried nanostructured cellulosic material which has been manufactured by a pulping process, and
   wherein the nanostructured cellulosic material has been modified to increase hydrophilicity or hydrophobicity of the cellulosic fibres by introducing or attaching charged functional groups on surfaces of the cellulosic fibres and/or has been modified to prevent or reduce aggregation of the composition during injection of the composition into a mammalian tissue.

26. A composition for use as a bulking agent, which is configured to be injected inside a wall of the urethra of a mammal or inside a wall of the rectum of a mammal, in the treatment of urinary or faecal incontinence respectively, the composition comprising a nanostructured cellulosic material,
   wherein the composition comprises 0.5 to 5.0 wt-% of the nanostructured cellulosic material and at least 95 wt-% water,
   wherein the nanostructured cellulosic material comprises never-dried nanostructured cellulosic material which has been manufactured by a pulping process, and
   wherein the nanostructured cellulosic material comprises nanostructured cellulosic material ionically cross-linked with metal ions.

\* \* \* \* \*